(12) United States Patent  (10) Patent No.: US 8,647,342 B2
Livneh  (45) Date of Patent: Feb. 11, 2014

(54) SURGICAL APPARATUS FOR TISSUE SEALING AND CUTTING

(75) Inventor: Steve Livneh, Amherstburg (CA)

(73) Assignee: Bovie Medical Corporation, Clearwater, FL (US)

(*) Notice: Subject to any disclaimer, the term of this patent is extended or adjusted under 35 U.S.C. 154(b) by 882 days.

(21) Appl. No.: 12/715,823

(22) Filed: Mar. 2, 2010

(65) Prior Publication Data

US 2010/0292690 A1   Nov. 18, 2010

Related U.S. Application Data

(60) Provisional application No. 61/156,643, filed on Mar. 2, 2009.

(51) Int. Cl.
*A61B 18/18*   (2006.01)
(52) U.S. Cl.
USPC .......... 606/51; 606/45; 606/52; 606/205; 606/206; 606/207
(58) Field of Classification Search
USPC .......... 606/39, 45, 49, 51, 52, 120, 148, 151, 606/159, 205–207, 210–212; 433/159; 81/345; 227/175.1–175.4, 180.1, 227/181.1, 182.1, 178.1, 179.1
See application file for complete search history.

(56) References Cited

U.S. PATENT DOCUMENTS

| 5,226,908 | A |   | 7/1993 | Yoon |
| 5,443,479 | A |   | 8/1995 | Bressi, Jr. |
| 5,507,297 | A |   | 4/1996 | Slater et al. |
| 5,603,723 | A | * | 2/1997 | Aranyi et al. ............... 606/205 |
| 5,611,808 | A |   | 3/1997 | Hossain et al. |
| 5,800,449 | A |   | 9/1998 | Wales |
| 5,820,630 | A | * | 10/1998 | Lind ............................ 606/208 |

(Continued)

FOREIGN PATENT DOCUMENTS

| EP | 1433428 A1 | 6/2004 |
| EP | 1557132    | 7/2005 |
| WO | 9507662 A1 | 3/1995 |

OTHER PUBLICATIONS

English language International Search Report for International Application No. PCT/US2010/025891, mailed Apr. 29, 2010; 2 pages.

(Continued)

*Primary Examiner* — Michael Peffley
*Assistant Examiner* — Khadijeh Vahdat
(74) *Attorney, Agent, or Firm* — Gerald E. Hespos; Michael J. Porco; Matthew T. Hespos

(57) ABSTRACT

A surgical apparatus for coagulating and cutting tissue includes a handle assembly having a housing. A tool cartridge is receivable in the housing. The tool cartridge includes a first jaw and a second jaw for grasping tissue therebetween. The first jaw is hingably movable between an open position and a closed position. A first jaw connection wire is operatively connected to the first jaw. A sheath encompasses at least part of the longitudinal portion of the jaw connection wire. A grip is disposed around at least part of the sheath. A piston is disposed within the sheath and operatively connected to the grip such that the grip and piston move in relation to one another. The jaw connection wire is operatively connected to the piston for moving the first jaw in response to movement of the grip.

19 Claims, 9 Drawing Sheets

(56) References Cited

U.S. PATENT DOCUMENTS

| | | |
|---|---|---|
| 6,099,550 A | 8/2000 | Yoon |
| 6,270,497 B1 | 8/2001 | Sekino et al. |
| 6,679,882 B1 * | 1/2004 | Kornerup .................... 606/51 |
| 2003/0191464 A1 | 10/2003 | Kidooka |
| 2004/0254573 A1 * | 12/2004 | Dycus et al. ................ 606/51 |
| 2008/0015566 A1 | 1/2008 | Livneh |
| 2008/0154299 A1 | 6/2008 | Livneh |
| 2008/0208246 A1 | 8/2008 | Livneh |

OTHER PUBLICATIONS

Written Opinion for International Application No. PCT/US2010/025891, mailed Apr. 29, 2010; 6 pages.

European Search Report for European Application No. 10749190.4; dated Nov. 9, 2012; five (5) pages.

International Search Report and Written Opinion for International Application No. PCT/US2010/001607, mailed Aug. 2, 2010; 7 pages.

\* cited by examiner

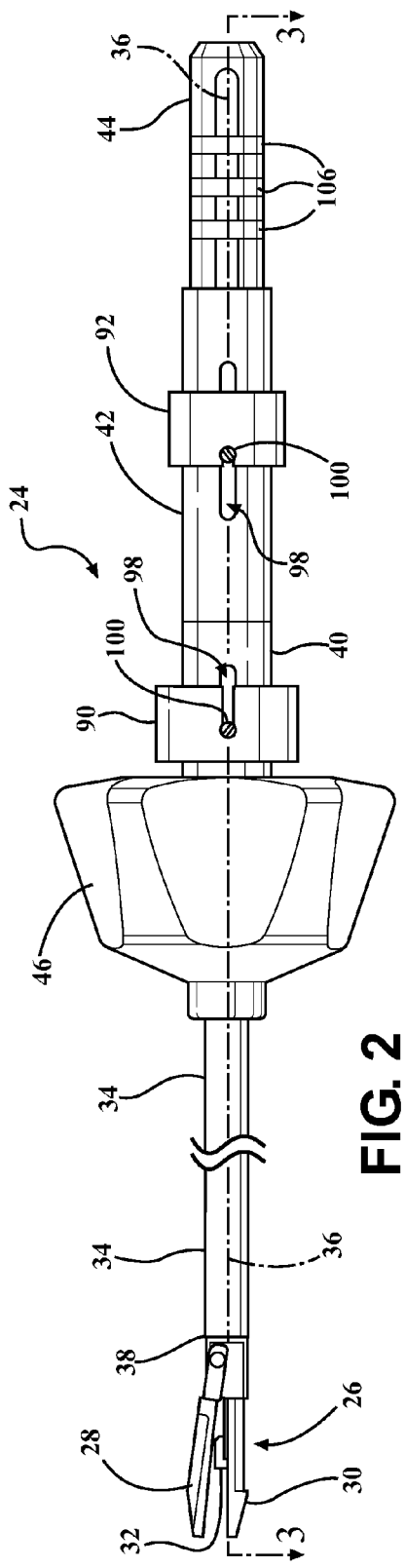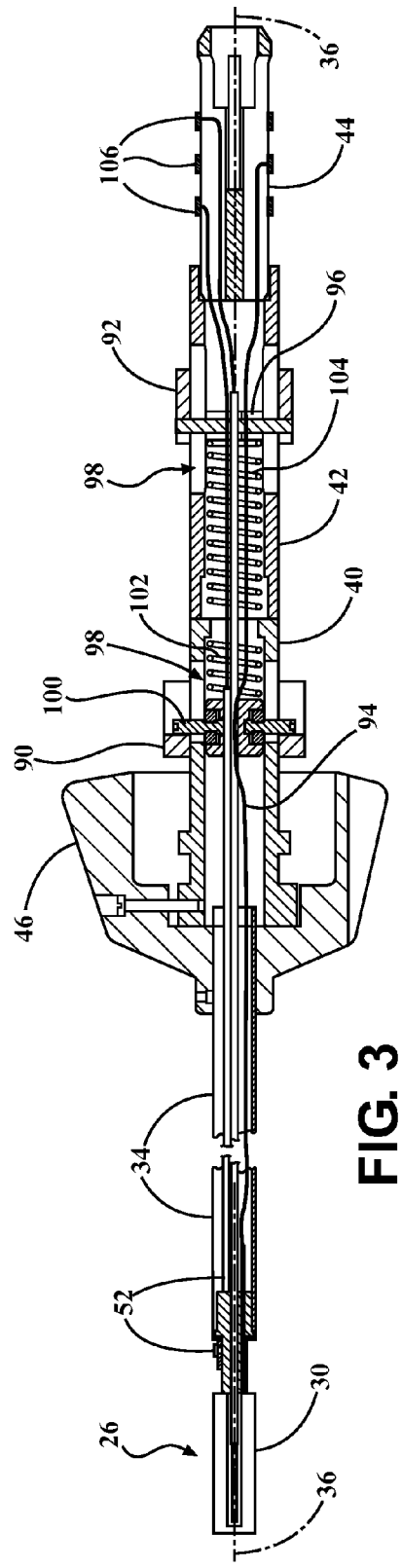

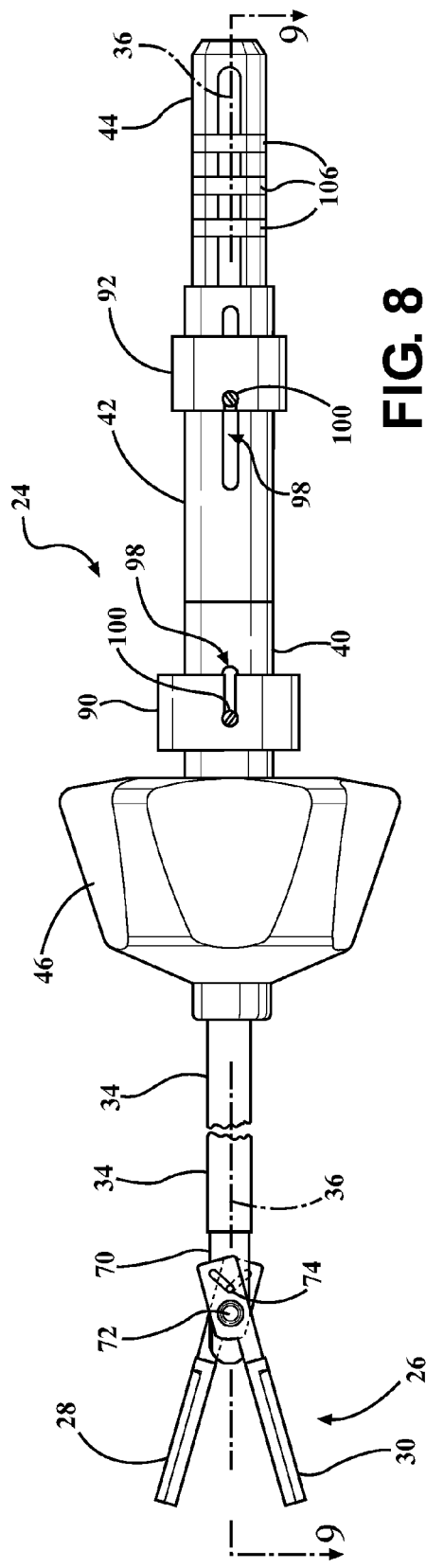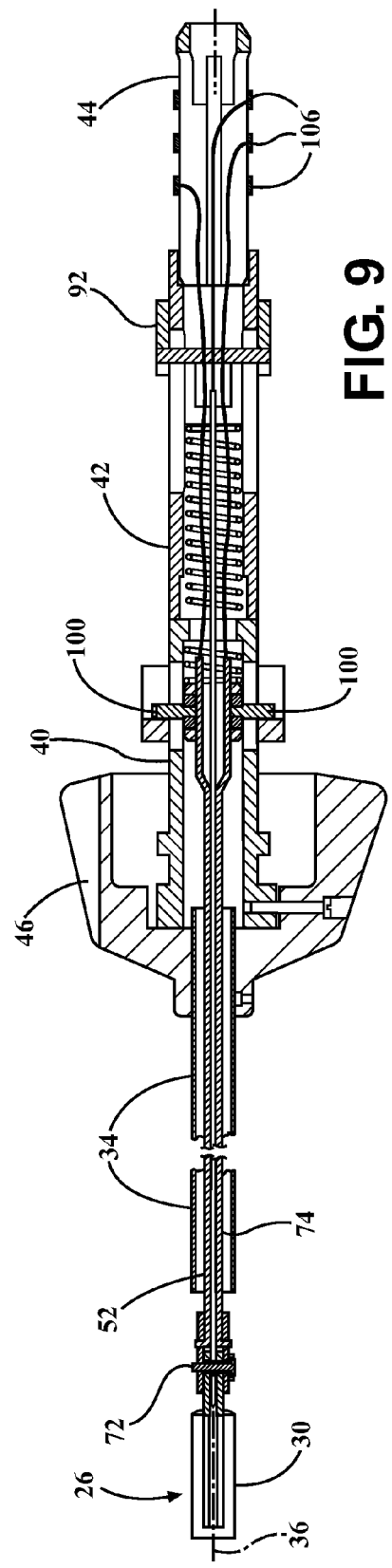

US 8,647,342 B2

SURGICAL APPARATUS FOR TISSUE SEALING AND CUTTING

CROSS REFERENCE TO RELATED APPLICATION

This application claims the benefit of provisional patent application No. 61/156,643, filed Mar. 2, 2009, which is hereby incorporated by reference.

BACKGROUND OF THE APPLICATION

The subject application relates generally to a surgical apparatus for tissue sealing and cutting.

SUMMARY OF THE INVENTION AND ADVANTAGES

The subject application discloses a surgical apparatus for coagulating and cutting tissue. The apparatus includes a handle assembly having a housing and a tool cartridge. The tool cartridge defines a longitudinal axis, the cartridge at least partially receivable and fully rotatable in the housing of the handle assembly. The tool cartridge includes a first jaw and a second jaw for grasping tissue therebetween where at least the first jaw is movable between an open position and a closed position. The first jaw includes an actuation portion and a grasping portion where the grasping portion extends longitudinally from the actuation portion. A first jaw connection wire is operatively connected to the actuation portion of the first jaw. A sheath encompasses at least part of the longitudinal portion of the jaw connection wire. A grip is disposed around at least part of the sheath and slidably engages the sheath. A piston is disposed within the sheath and operatively connected to the grip such that the grip and piston move in relation to one another. The jaw connection wire is operatively connected to the piston for moving the first jaw in response to movement of the grip. The handle assembly further includes a jaw actuation lever operatively engagable with the grip of the tool cartridge such that the grip and the first jaw connection wire move to actuate the first jaws in relation to actuation of the jaws actuation lever.

By utilizing the jaw connection wire, the surgical apparatus allows for smooth and tactilely responsive operation of the jaws by a surgeon or other user of the apparatus.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 2 is a side view of a tool cartridge of a first embodiment;

FIG. 3 is a cross sectional view of the tool cartridge of the first embodiment along line 3-3 in FIG. 2;

FIG. 8 is a side view of the tool cartridge of a second embodiment;

FIG. 9 is a cross sectional view of the tool cartridge of the second embodiment;

DETAILED DESCRIPTION OF THE INVENTION

Referring to the Figures, wherein like numerals indicate like parts throughout the several views, a surgical apparatus 20 is shown herein. The surgical apparatus 20 of the illustrated embodiment may be used for coagulating (i.e., sealing) and cutting tissue, such as blood vessels, using electrical energy. However, other uses of the surgical apparatus 20 described hereafter will be realized by those skilled in the art.

Figure 1:
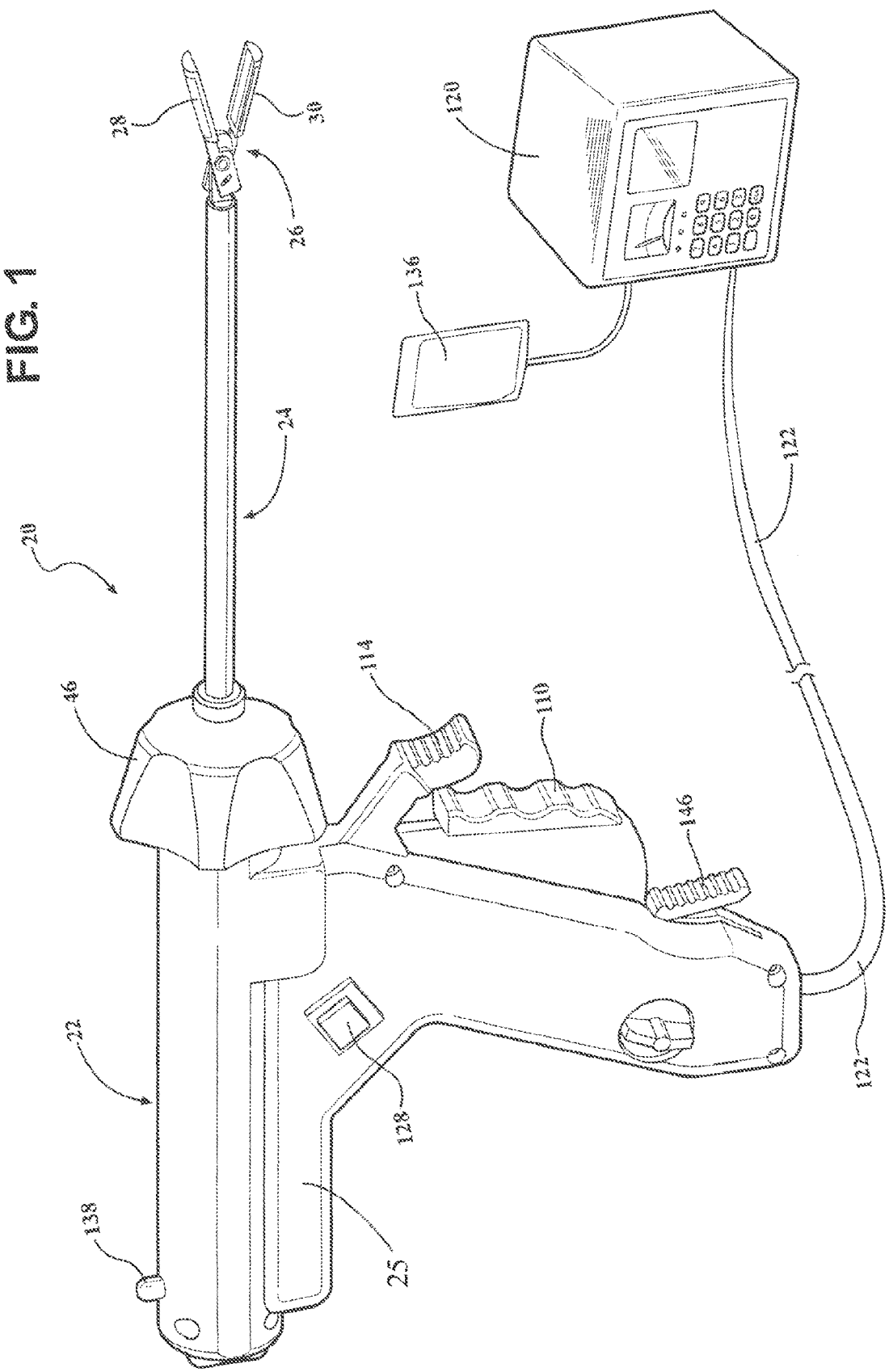
FIG. 1 is a perspective view of a surgical apparatus having a handle assembly supporting a tool cartridge and showing connection to a power source.
Figure 15:
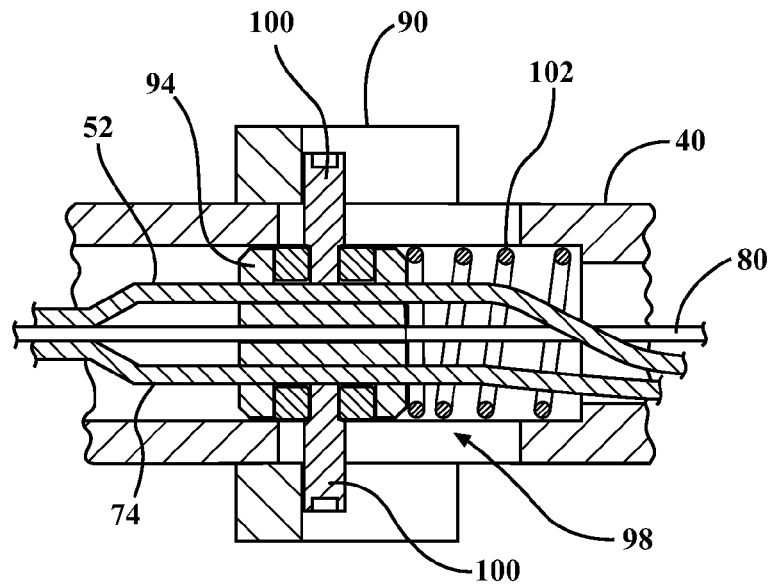
FIG. 15 is a cross sectional view of part of the tool cartridge of the second embodiment showing the first grip and the first piston securing the jaw connection wires.
Figure 16:
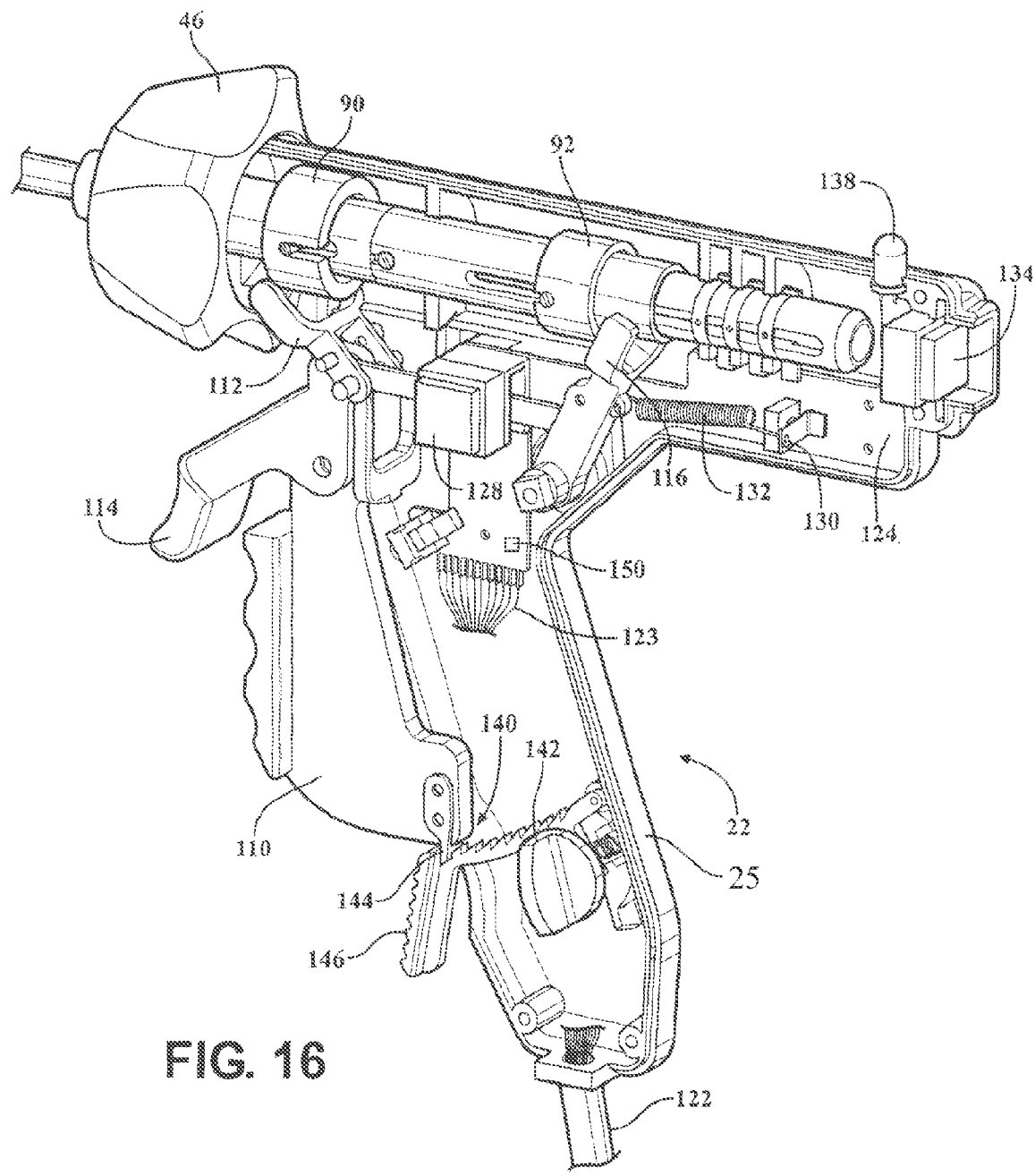
FIG. 16 is a perspective view of an interior of a housing of the handle assembly and part of the tool cartridge.
Figure 17:
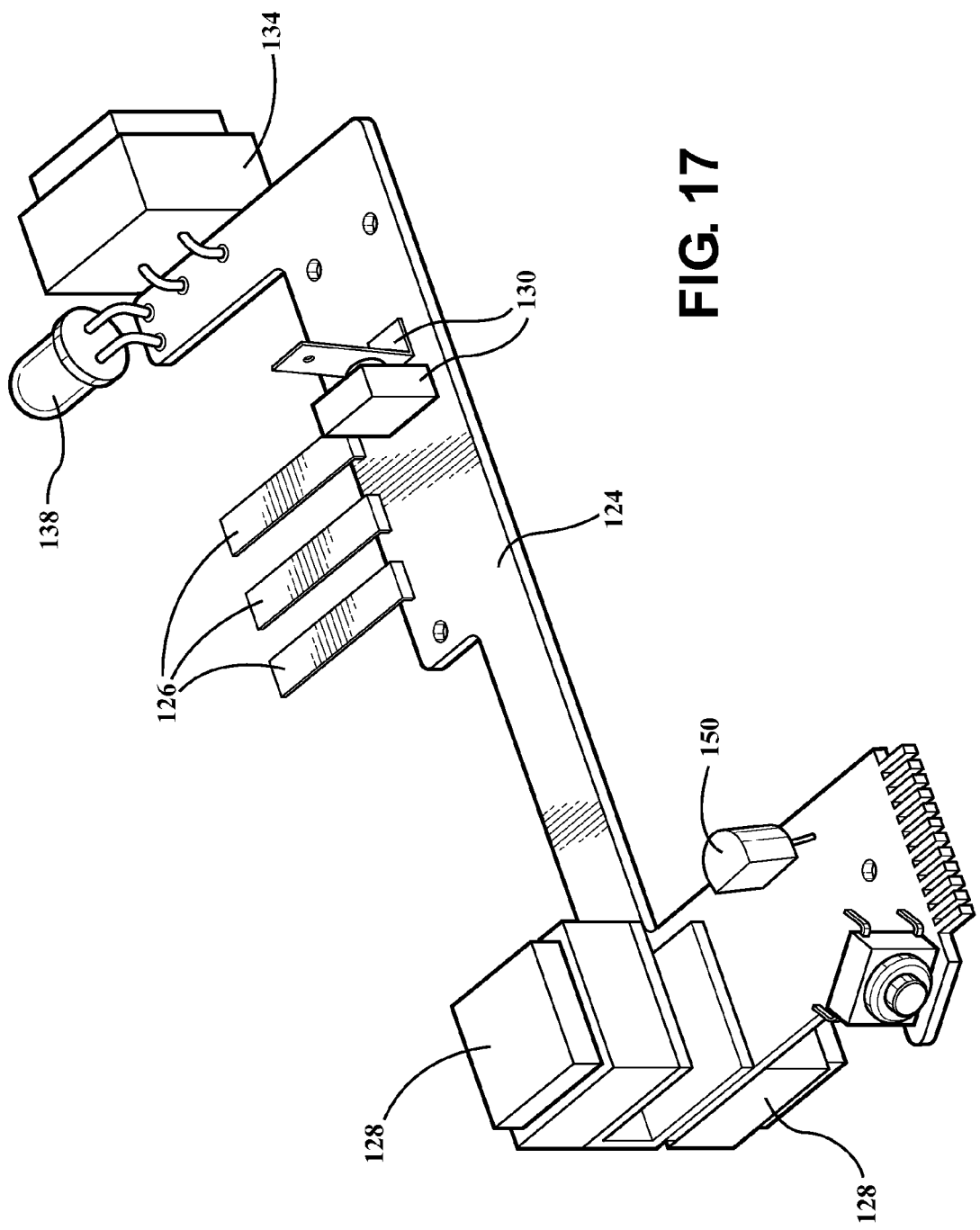
FIG. 17 is a perspective view of a printed circuit board disposed in the housing of the handle assembly.

Referring to FIGS. 1 and 16, the surgical apparatus 20 includes a handle assembly 22 accommodating a tool cartridge 24. Two illustrative embodiments for the tool cartridge 24 are shown herein. Specifically, a first embodiment is shown in FIGS. 2-7 and a second embodiment is shown in FIGS. 8-15. Of course, other embodiments of the tool cartridge 24 and handle assembly 22 may be contemplated by those skilled in the art in light of the teachings herein.

The handle assembly 22 includes a housing 25. The tool cartridge 24 is at least partially receivable in the housing 25 of the handle assembly 22. That is, the housing 25 supports the tool cartridge 24 by interfacing with at least part of the tool cartridge 24. Specifically, in the illustrated embodiments, part of the tool cartridge 24 is disposed inside the housing 25 and part of the tool cartridge 24 is disposed outside the housing 25.

Referring to FIGS. 2-5 and 8-12, the tool cartridge 24 includes at least one tool 26 for operating on the tissue. In the illustrated embodiments, the at least one tool 26 is implemented as a first jaw 28, a second jaw 30, and a blade 32. The first and second jaws 28, 30 are used to grasp the tissue while the blade 32 is used to cut the tissue. The jaws 28, 30 and the blade 32 are preferably formed of conductive material, such as metal, to allow them to be used to apply electrical energy to the tissue, as described in greater detail below. However, it is also preferred that the jaws 28, 30 and the blade 32 are at least partially formed of, or coated with, an insulating material 33, such that electrical energy is applied primarily to the tissue that is being operated on.

Referring to FIGS. 2, 3, 8, and 9, the tool cartridge 24 includes at least one sheath (not separately numbered) for providing structural support for the tool cartridge 24 and enclosing certain components (not separately numbered) as described in detail below. An extension sheath 34 extends along a longitudinal axis 36 between a proximal end (not numbered) and a distal end 38. The at least one tool 26 is supported by the extension sheath 34 and extends from the distal end 38. The tool cartridge 24 of the illustrated embodiment also includes a first sheath 40, a second sheath 42, and a third sheath 44 extending along the longitudinal axis 36. The extension sheath 34 is coupled to the first sheath 40, the second sheath 42 is coupled to the first sheath 40, and the third sheath 44 is coupled to the second sheath 42. Although the sheaths 34, 40, 42, 44 of the illustrated embodiment are formed of separate components that are coupled together, those skilled in the art realize that the sheaths 34, 40, 42, 44 could be formed in a unitary matter, i.e., a one-piece construction. The first, second, and third sheaths may be formed of any suitable material, including, but not limited to, metal, plastic, or fiberglass.

The sheaths 34, 40, 42, 44 of the illustrated embodiment have a tubular or cylindrical shape. This shape allows the tool cartridge 24 to fully rotate about the longitudinal axis 36 while supported by the handle assembly 22. However, those skilled in the art contemplate other functional shapes for the sheaths 34, 40, 42, 44. The tool cartridge 24 of the illustrated embodiment further includes a knob 46 supported by the extension and first sheaths 34, 40. The knob 46 allows the user of the apparatus 20 to rotate the tool cartridge 24, and thus rotate the tools 26.

As stated above, the first jaw 28 and the second jaw 30 allow for the grasping of tissue between the jaws 28, 30. As such, at least one of the jaws 28, 30 is movable with respect to the other. In a first embodiment, as shown best in FIGS. 2-5, the second jaw 30 is fixed while the first jaw 28 is movable between an open position and a closed position. In a second embodiment, as shown best in FIGS. 8-12, both jaws 28, 30 are movable between an open position and a closed position for grasping the tissue therebetween.

In the illustrated embodiments, each of the jaws 28, 30 include an actuation portion 48 and a grasping portion 50 extending longitudinally from the actuation portion 48. The grasping portion 50 is used to interface with and grasp the tissue and the actuation portion assist in movement of the jaw or jaws 28, 30.

Figure 4:
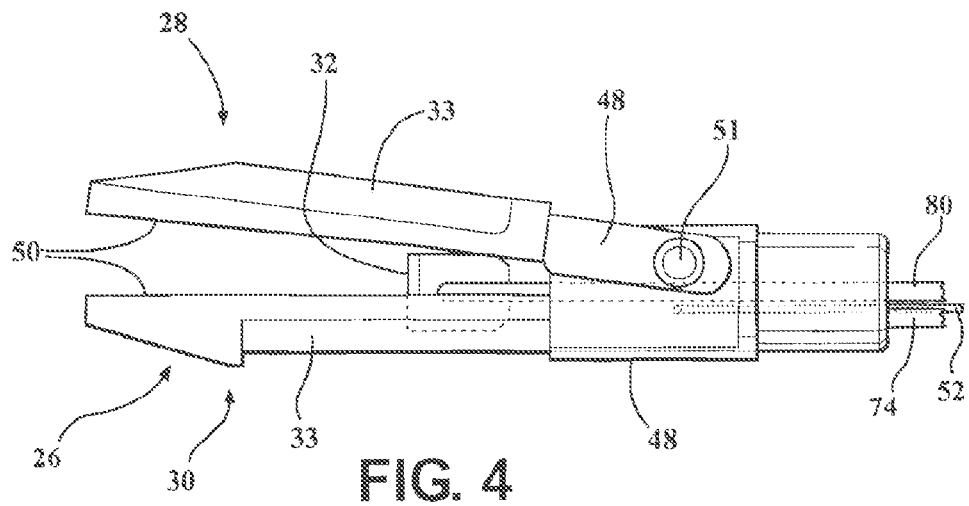
FIG. 4 is a side view of jaws and a blade of the tool cartridge of the first embodiment.
Figure 5:
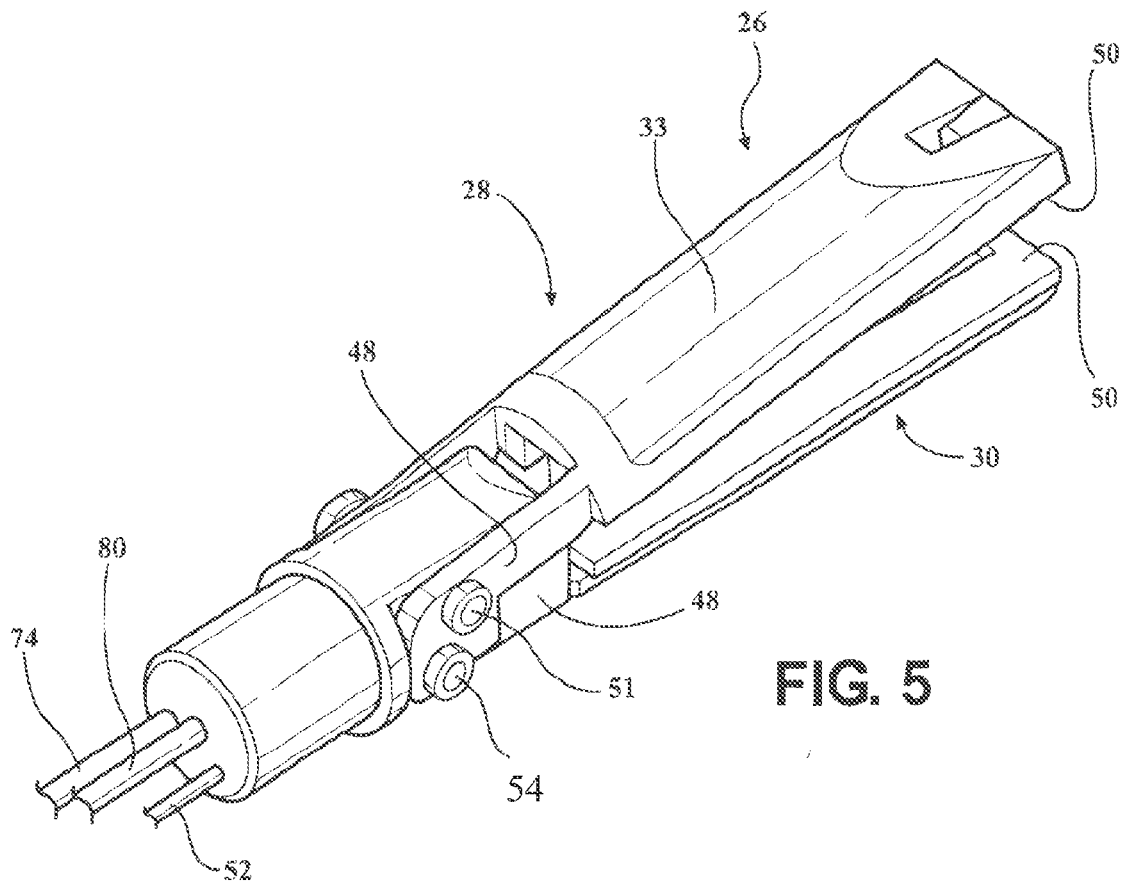
FIG. 5 is a perspective view of the jaws and the blade of the tool cartridge of the first embodiment.

In the first embodiment, as best seen in FIGS. 4 and 5, the actuation portion 48 of the first jaw 28 is hingably connected to the actuation portion 48 of the second jaw 30. More specifically, the actuation portion 48 of the first jaw 28 is forked with a pair of legs (not numbered) positioned on either side of the actuation portion 48 of the second jaw 30. A pin 51 is disposed through holes (not numbered) in the actuation portions 48 of the jaws 28, 30 such that the first jaw 28 may pivot about the pin 51.

A first jaw connection wire 52 is operatively connected to the first jaw 28. This wire 52 extends away from the first jaw 28, such that when pulled, the first jaw 28 pivots about the pin 51 and moves from the open position to the closed position. As such, the wire 52, which could also be referred to as a rod, has the necessary rigidity to actuate the first jaw 28. Specifically, in the first embodiment, the first jaw connection wire 52 defines a proximal end (not numbered) and a distal end 54 and includes a longitudinal portion 56 generally parallel to the longitudinal axis 36 and a lateral portion 58 generally perpendicular to the longitudinal axis 36. The lateral portion 58 is defined adjacent the distal end 54 and interfaces with a hole (not numbered) in the actuation portion 48 of the first jaw 28.

In the illustrated first embodiment, the lateral portion 58 is secured to the actuation portion 48 of the first jaw 28.

In the second embodiment, as best seen in FIGS. 10-13, the actuation portion 48 of the first jaw 28 is hingably connected to the actuation portion 48 of the second jaw 30. More specifically, a linking part 70 is utilized to hingably link the jaws 28, 30 together and operatively connect them to the extension sheath 34. The linking part 70 is connected to the extension sheath and defines a pair of holes (not numbered) for accommodating a pin 72. The pin 72 is also disposed through holes (not numbered) defined in the actuation portion 48 of each jaw 28, 30. As such, each jaw 28, 30 pivots about the pin 72 between the open position and the closed potion.

Figure 10:
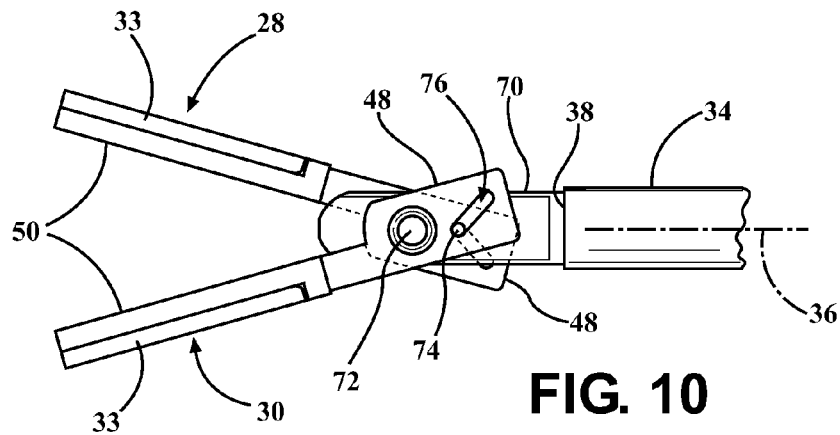
FIG. 10 is a side view of part of the tool cartridge of the second embodiment showing the jaws in an open position.
Figure 13:
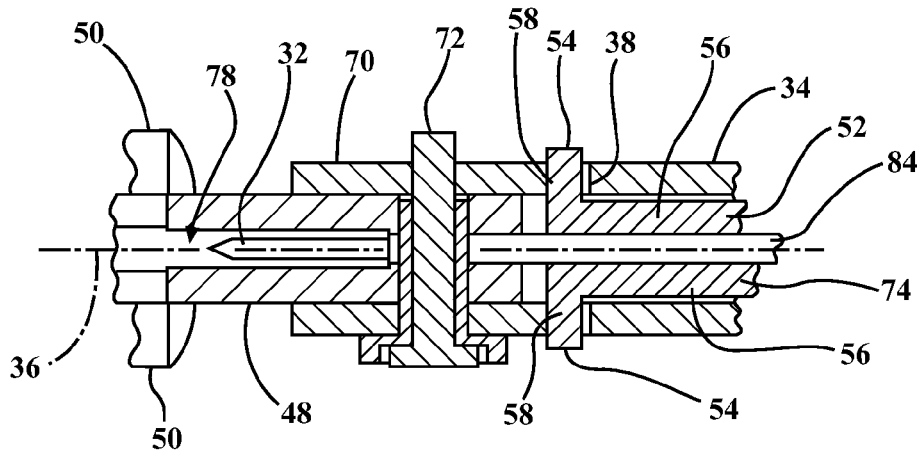
FIG. 13 is a cross-sectional view of part of the tool cartridge of the second embodiment showing connection of connection wires to actuation portions of the jaws.

A first jaw connection wire 52 is operatively connected to the first jaw 28 and a second jaw connection wire 74 is operatively connected to the second jaw 30. These wires 52, 74 extend away from the jaws 28, 30, such that when pulled, the jaws 28, 30 pivot about the pin 72 and move from the open position to the closed position. Specifically, in the second embodiment, and as shown in FIG. 13, each jaw connection wire 52, 74 defines a proximal end (not numbered) and a distal end 54 and includes a longitudinal portion 56 generally parallel to the longitudinal axis 36 and a lateral portion 58 generally perpendicular to the longitudinal axis 36. The lateral portion 58 is defined adjacent the distal end 54. Referring to FIG. 10, each actuation portion 48 of the jaws 28, 30 defines a slot 76. Each slot 76 is disposed at an angle with respect to the longitudinal axis 36 when the jaws are in the open position. That is, the slots 76 are non-parallel to the longitudinal axis 36 when the jaws 28, 30 are in the open position. The lateral portion 58 of the wires 52, 74 interface with the respective slots 76 of the first and second jaws 28, 30. When the wires 52, 74 are pulled, each lateral portion 58 slides along the respective slot 76. The jaws 28, 30 pivot about the pin 72 and are actuated toward the closed position. The angle of the slots 76 are opposite one another such that the jaws 28, 30 move toward one another. The wires 52, 74 have the necessary rigidity to actuate the jaws 28, 30 as is realized by those skilled in the art.

The jaw connection wires 52, 74 of the illustrated embodiments extend away from the jaws 28, 30 and are enclosed within the sheaths 34, 40, 42, 44. The jaw connection wires 52, 74 are preferably formed of a conductive material such that they may carry electrical current to the jaws 28, 30. It is also preferred that at least a portion of the jaw connection wires 52, 74 are surrounded by an insulating material. By utilizing the jaw connection wires 52, 74, the surgical apparatus allows for smooth and tactilely responsive operation of the jaws 28, 30 by a surgeon or other user of the apparatus 20, while still allowing electrical conduction to the jaws 28, 30.

Figure 6:
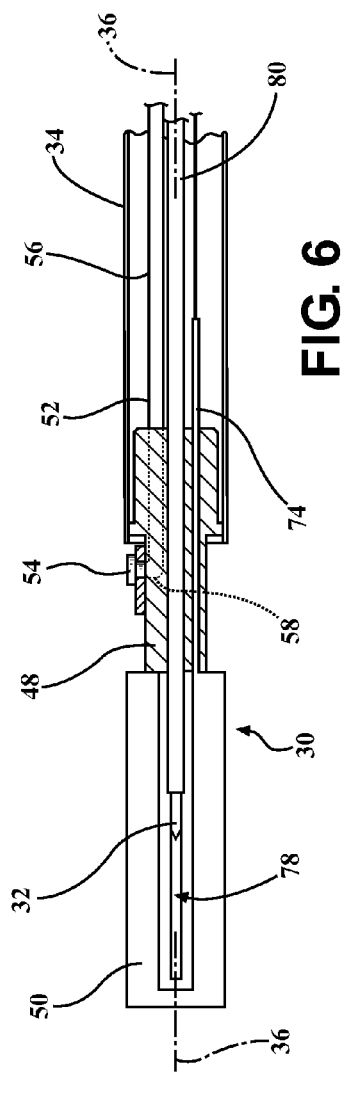
FIG. 6 is a cross sectional view of part of the tool cartridge of the first embodiment showing the jaws and the blade supported by the extension sheath.
Figure 11:
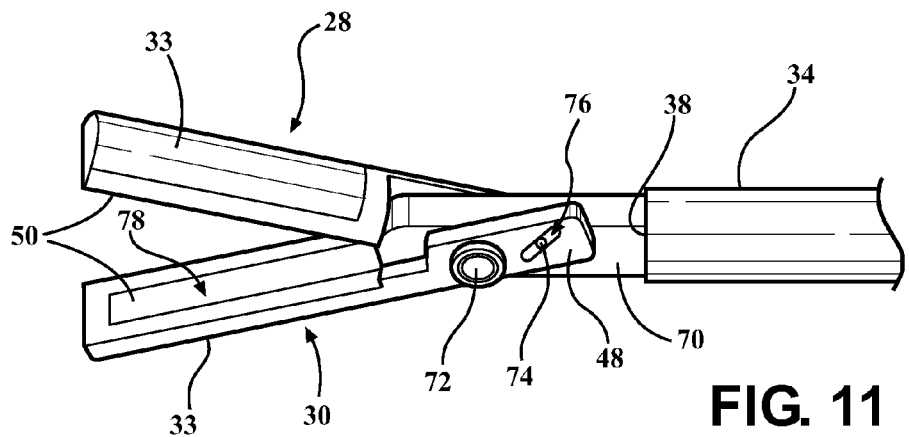
FIG. 11 is a perspective view of part of the tool cartridge of the second embodiment showing the jaws in the open position.
Figure 12:
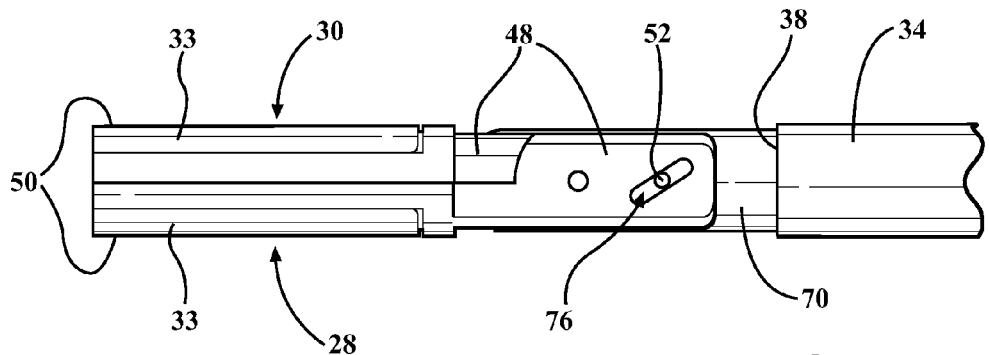
FIG. 12 is a side view of part of the tool cartridge of the second embodiment showing the jaws in a closed position.

In the illustrated embodiments, and as shown in FIGS. 6, 11, and 13, the jaws 28, 30 each define a channel 78 for accommodating the blade 32. That is, when the jaws 28, 30 are in the closed position, the blade 32 may slide generally unencumbered between the jaws 28, 30.

Figure 14:
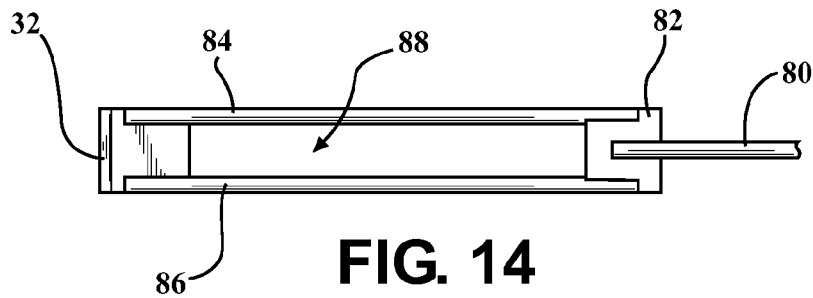
FIG. 14 is a side view of the blade and stanchions of the second embodiment.

Referring to FIGS. 3-6, 9, 13, and 14, a blade connection wire 80 is operatively connected to the blade 32 such that movement of the blade connection wire 80 corresponds to movement of the blade 32. In the first embodiment, the blade connection wire 80 is connected to the blade 32. In the second embodiment, as best shown in FIG. 14, the blade connection wire 80 is connected to a plate 82. An upper stanchion 84 and a lower stanchion 86 are connected to the plate 82 and define a gap 88 therebetween. The blade 32 is connected to the upper and lower stanchions 84, 86. The gap accommodates the pin 72 while allowing free movement of the blade 32.

The blade connection wire 80 of the illustrated embodiments extends away from the jaws 28, 30 and the blade 32 and is enclosed within the sheaths 34, 40, 42, 44. The blade connection wire 80 is preferably formed of a conductive material such that it may carry electrical current to the blade 32. It is also preferred that at least a portion of the blade connection wire 80 is surrounded by an insulating material.

Referring to FIGS. 2, 3, 8, and 9, the tool cartridge 24 further includes a first grip 90 operatively connected to at least one of the jaw connection wires 52, 74 for actuating movement of at least one of the jaws 28, 30. The tool cartridge 24 also includes a second grip 92 operatively connected to the blade connection wire 80 for actuating movement of the blade 32. When the tool cartridge 24 is properly integrated with the handle assembly 22, the first and second grips 90, 92 are disposed within the housing 26. In the illustrated embodiment, the first grip 90 is disposed around and slidably engages the first sheath 40 and the second grip 92 is disposed around and slidably engages the second sheath 42. Also in the illustrated embodiments, the grips 90, 92 are ring shaped such that they permit the cartridge 24 to be rotated and are engagable at any rotational position. However, those skilled in the art realize alternative shapes and locations for the grips 90, 92.

Figure 7:
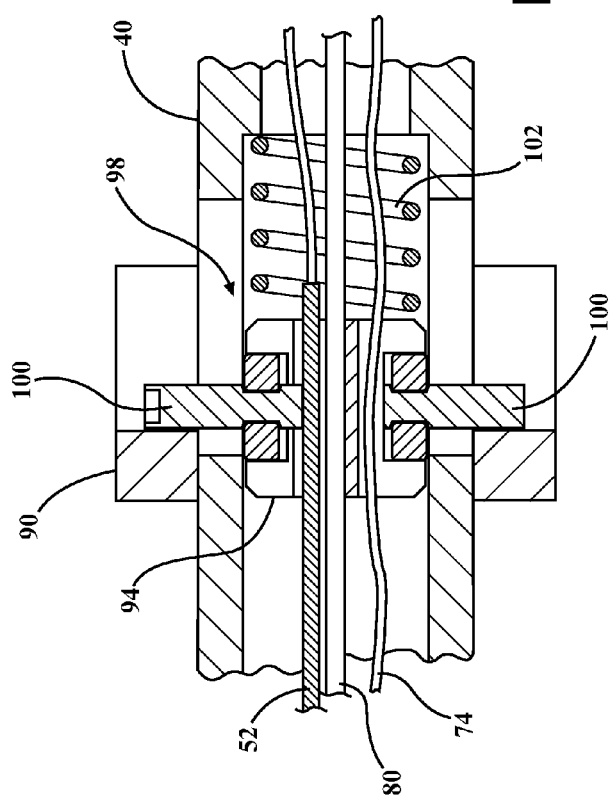
FIG. 7 is a cross sectional view of part of the tool cartridge of the first embodiment showing a first grip and a first piston securing a first jaw connection wire.

In the illustrated embodiments, a first piston 94 is disposed within the first sheath 40 and a second piston 96 is disposed within the second sheath 42, as shown in FIGS. 3 and 9. The first piston 94, shown in detail in FIGS. 7 and 15, is operatively connected to at least one of the jaw connection wires 52, 74 and the first grip 90. Accordingly, the at least one jaw connection wire 52, 74, the first grip 90, and the first piston 94 move in relation with one another. The second piston 96 is operatively connected to the blade connection wire 80 and the second grip 92. Accordingly, the blade 32, the blade connection wire 80, the second grip 92, and the second piston 96 move in relation with one another. Specifically, in the illustrated embodiments, each piston 94, 96 defines three channels (not numbered) for accommodating the connection wires 52, 74, 80. In the illustrated embodiments, each channel is defined completely through each piston 94, 96. Furthermore, in the illustrated embodiment each piston 94, 96 is cylindrically shaped. However, other appropriate shapes for the pistons 94, 96 will be realized by those skilled in the art.

In the illustrated embodiments, the first and second sheaths 40, 42 each define at least one slit 98. At least one screw 100 (or pin) is disposed through each slit 98 and interconnects the first piston 94 to the first grip 90 and the second piston 96 to the second grip 92. Furthermore, the screws 100 also compress against the respective wires 52, 74, 80. Specifically, in the first embodiment, one screw 100 secures the first jaw connection wire 52 to the first piston 94 and one screw 100 secures the blade connection wire 80 to the second piston 96. In the second embodiment, one screw 100 secures the first jaw connection wire 52 to the first piston 94, one screw 100 secures the second jaw connection wire 74 to the first piston 94, and one screw 100 secures the blade connection wire 80 to the second piston 96. Of course, techniques for linking the pistons 94, 96 and sheaths 40, 42, other than described above, may be realized by those skilled in the art. Furthermore, it should also be appreciated that a length of each slit 98 limits the motion of the pistons 94, 96 and grips 90, 92 and thereby regulates the motion of the jaws 28, 30 and the blade 32.

The tool cartridge 24 further includes a first spring 102 operatively engagable with the first piston 94 and a second spring 104 operatively engagable with the second piston 96. The first spring 102 biases the first piston 94 forward in the first sheath 40, and thereby biases the jaws 28, 30 towards the open position. The second spring 104 biases the second piston 96 backward in the second sheath 42, and thereby biases the blade 32 away from the jaws 28, 30.

Still referring to FIGS. 2, 3, 8, and 9, the tool cartridge 24 also includes at least one conductive areas 106 preferably disposed on an exterior (not separately numbered) of the third sheath 44. The conductive areas 106 in the illustrated embodiments are ring shaped such that electrical contact can be made with the conductive areas 106 at any rotational position of the tool cartridge 24. Specifically, in the illustrated embodiment, three conductive areas 106 are utilized. Each of the wires 52, 74, 80 is electrically connected to one of the conductive areas 106. As such, each wire 52, 74, 80 electrically connects the jaws 28, 30 and the blade 32 to one conductive area 106.

Referring to FIGS. 1 and 16, the handle assembly 22 includes a jaw actuation lever 110. The jaw actuation lever 110 is preferably pivotably hinged to allow motion about a pin (not numbered). The jaw actuation lever 110 is operatively engagable with the first grip 90 of the tool cartridge 24. Accordingly, depression of the jaw actuation lever 110 moves the first grip 90 to actuate the jaws 28, 30 in relation to actuation of the jaw actuation lever 110.

The jaw actuation lever 110 is positioned both inside and outside of the housing 25 such that a user of the apparatus 20 may actuate the jaw actuation lever 110. Preferably, the jaw actuation lever 110 includes a first forked part 112 extending thereof. The first forked part 112 contacts the first grip 90. When the jaw actuation lever 110 is depressed, the first forked part 112 pushes the first grip 90 backward, i.e., away from the jaws 28, 30, thus placing the first spring 102 under additional tension. This movement of the first grip 90 forces the jaws 28, 30 towards their closed position.

The handle assembly 22 also includes a blade actuation lever 114. The blade actuation lever 114 is preferably pivotably hinged. In the illustrated embodiments, the blade actuation lever 114 is operatively connected to the second grip 92 of the tool cartridge 24. Accordingly, depression of the blade actuation lever 114 moves the second grip 92 and the blade connection wire 80 to actuate the blade 32 in relation to actuation of the blade actuation lever 114.

The blade actuation lever 114 is positioned both inside and outside of the housing 25 such that the user of the apparatus 20 may actuate the blade actuation lever 114. A second forked part 116 is operatively connected to blade actuation lever 114. The second forked part 116 contacts the second grip 92 to effectuate movement of the second grip 92. Specifically, when the blade actuation lever 114 is depressed, the second forked part 116 pushes the first grip 90 forward, i.e., towards from the jaws 28, 30, thus placing the second spring 104 under additional compression. This movement of the second grip 92 forward forces the blade 32 towards the jaws 28, 30.

The handle assembly 22 is electrically connectable to a power source 120 via a cable 122. The cable 122 preferably includes a plurality of conductors 123 for conduction of electrical power and/or data between the handle assembly 22 and the power source 120.

The handle assembly 22 may include a printed circuit board (PCB) 124 disposed within the housing 25. In the illustrated embodiments, the conductors of the cable 122 are electrically connected to the PCB 124. A plurality of electrical contacts 126 are electrically connected to and supported by the PCB 124. The electrical contacts 126 make contact with the conductive areas 106 of the tool cartridge 24.

The handle assembly 22 further includes a power switch 128 electrically connected to the PCB 124 for initiating conduction of electrical power from the power source 112 to the jaws 28, 30 and/or the blade 32. The power switch 128 is preferably a pushbutton to allow the user of the apparatus 20 to initiate electrical power after closing the jaws 28, 30 on the tissue.

The handle assembly 22 also preferably includes a cut-coag switch 130. The cut-coag switch 130 is preferably disposed within the housing 25 and is operatively connected to the second forked part 116. Thus, the cut-coag switch 130 is operatively connected to the blade actuation lever 114 as well. In the illustrated embodiments, such as is shown in FIG. 16, an extension spring 132 connects the cut-coag switch 130 to the second forked part 116. The cut-coag switch 130 is electrically connected to the PCB 124 for switching the apparatus 20 between a coagulating mode and a cutting mode, as described in detail below. As the cut-coag switch 130 is preferably disposed within the housing 25 it is not directly activated by a surgeon, but rather by operation of the blade actuation lever 114.

In bipolar operation, the apparatus 20 includes a coagulation mode and a cutting mode. When operating on the tissue, the coagulation mode is typically performed first to coagulate the blood and tissue proteins. As such, the blade 32 is retracted. Accordingly, the cut-coag switch 130 is not activated, i.e., the switch 130 is open. Therefore, in the coagulation mode, i.e., when the cut-coag switch 130 is not activated, electric current flows from one of the jaws 28, 30 to the other of the jaws 30, 28.

After performing coagulation of the tissue, the surgeon proceeds to cut the tissue. Using the apparatus 20, the surgeon will advance the blade 32 using the blade actuation lever 114 (which, in turn, operates the second forked part 116). As the second forked part 116 is moved forward, the extension spring 132 activates the cut-coag switch 130. This turns the apparatus 20 into cutting mode. As such, the electric current is then conducted from the blade 32, through the tissue, to the jaws 28, 30. This allows for superior cutting as both the sharp edge of the blade 32 and the electric current operate in tandem to cut the tissue.

The electric waveform and cycle timing is typically different in the coagulation mode than in the cutting mode. For instance, in the coagulation mode, a pulsed RF waveform at a first frequency is typically used (e.g., 0.2 seconds on, and 0.8 seconds off). In the cutting mode, a constant RF waveform at a second frequency, different than the first frequency, is typically used. Those skilled in the art realize numerous techniques to produce suitable waveforms and cycle timing for the differing modes.

The handle assembly 22 may also include a polarity switch 134 electrically connected to the PCB 124. The polarity switch 134 allows selection of either monopolar or bipolar operation of the apparatus 20. Bipolar operation is described above with respect to either the coagulation mode or the cutting mode. In monopolar operation, electric current is conducted from the jaws 28, 30 and the blade 32, through the tissue, to a conductive pad 136. Those skilled in the art realized that the conductive pad 136 is often referred to as a "ground pad". The conductive pad 136 is placed in contact with the body of the patient on whom the surgery is being performed such that a circuit is completed through the body of the patient.

By allowing convenient access to monopolar mode, the surgeon can easily switch the apparatus 20 from bipolar to monopolar (and back again if necessary) to complete the cutting operation. This on-the-fly switching is particularly useful for cutting "hard-to-cut" tissue, which is often only realized during the middle of a coagulation and cutting procedure.

The handle assembly 22 may further include a light 138, such as a light emitting diode (LED). The light 138 is electrically connected to the PCB 124. In some embodiments, the light illuminates when the apparatus 20 is in monopolar operation.

The handle assembly 22 may also include a lever locking assembly 140. As best shown in FIG. 16, the lever locking assembly 140 is used to retain the jaw actuation lever 110 in position. The lever locking assembly 140 includes a plurality of teeth 142 in a saw-tooth configuration. The teeth 142 interface with a pin 144 extending from the jaw actuation lever 110. As the jaw actuation lever 110 is depressed, the pin 144 latches against one of the teeth 142. This holds the jaw actuation lever 110 (and accordingly the jaws 28, 30) in position such that the surgeon need not retain pressure on the jaw actuation lever 110. The lever locking assembly also includes a tab 146 extending from the teeth 142 and positioned outside of the housing 26 to allow release of the pin 144 from the teeth 142.

The handle assembly 22 and/or the tool cartridge 24 may also include an identification chip 150. In the illustrated embodiment, the identification chip 150 is supported by the PCB 124, as is shown in FIG. 16. The chip 150 contains identification data to identify the handle assembly 22 and/or tool cartridge 24 that is that is connected to the power source 120. Particularly, the identification data may include a serial number, the particular tools 26 that the cartridge 24 carries, or other relevant information. The power source 120 may track the serial numbers provided by the identification chip 150 to limit the number of uses of each particular tool cartridge 24 and/or handle assembly 22. The power source 120 may also launch an initial default setup to accommodate the characteristics of the specific tool cartridge 24 and/or apparatus 20.

The present invention has been described herein in an illustrative manner, and it is to be understood that the terminology which has been used is intended to be in the nature of words of description rather than of limitation. Obviously, many modifications and variations of the invention are possible in light of the above teachings. The invention may be practiced otherwise than as specifically described within the scope of the appended claims.

What is claimed is:

1. A surgical apparatus for coagulating and cutting tissue, said apparatus comprising:
   a handle assembly including a housing;
   a tool cartridge defining a longitudinal axis, said cartridge at least partially receivable in said housing of said handle assembly;
   said tool cartridge including:
      a first jaw and a second jaw for grasping tissue therebetween wherein at least said first jaw is hingably movable between an open position and a closed position,
      said first jaw including an actuation portion and a grasping portion wherein said grasping portion extends longitudinally from said actuation portion,
      a first jaw connection wire operatively connected to said actuation portion of said first jaw,
      a substantially cylindrical sheath encompassing at least part of said first jaw connection wire, wherein a side portion of the substantially cylindrical sheath includes a longitudinal slit,
      a grip disposed around at least part of said sheath and slidably engaging said sheath, and
      a piston disposed within said sheath and operatively connected to said grip such that said grip and piston move in relation with one another, said piston being connected to said grip by a pin slideable within said longitudinal slit of said sheath, wherein a slideable movement of said grip with respect to said sheath is limited by a slideable movement of said pin within said slit, and said first jaw connection wire being operatively connected to said piston for moving said first jaw in response to movement of said grip; and said handle assembly further including a jaw actuation lever operatively engagable with said grip of said tool cartridge such that said grip and said first jaw connection wire move to actuate said first jaws in relation to actuation of said jaws actuation lever.

2. A surgical apparatus as set forth in claim 1 wherein said first jaw connection wire includes a longitudinal portion generally parallel to said longitudinal axis and a lateral portion generally perpendicular to said longitudinal axis.

3. A surgical apparatus as set forth in claim 2 wherein said lateral portion interfaces with a hole defined in said actuation portion of said first jaw.

4. A surgical apparatus as set forth in claim 2 wherein said second jaw includes an actuation portion and a grasping portion wherein said grasping portion extends longitudinally from said actuation portion.

5. A surgical apparatus as set forth in claim 4 wherein said actuation portions of said jaws each define a slot.

6. A surgical apparatus as set forth in claim 5 wherein said lateral portion of said first jaw connection wire is disposed within said slot of said first jaw.

7. A surgical apparatus as set forth in claim 6 further comprising a second jaw connection wire having a longitudinal portion generally parallel to said longitudinal axis and a lateral portion generally perpendicular to said longitudinal axis and wherein said lateral portion of said second jaw connection wire is disposed with said slot of said second jaw.

8. A surgical apparatus as set forth in claim 7 further comprising a linking part operatively connected to said sheath and operatively connected to said actuation portions of said jaws.

9. A surgical apparatus as set forth in claim 7 wherein a length of said slots of each of said jaws is non-parallel with said longitudinal axis when said jaws are in the open position.

10. An apparatus as set forth in claim 1 further comprising a spring disposed within said sheath for engaging said piston and biasing said first jaw towards said open position.

11. An apparatus as set forth in claim 1 wherein said piston is cylindrically shaped and defining at least one channel extending at least partially therethrough.

12. An apparatus as set forth in claim 11 wherein said jaw connection wire is disposed in said at least one channel and secured to said piston with said pin.

13. An apparatus as set forth in claim 11 further comprising a blade movable between said jaws.

14. An apparatus as set forth in claim 13 further comprising a blade connection wire operatively connected to said blade such that movement of said blade connection wire corresponds to movement of said blade.

15. An apparatus as set forth in claim 14 wherein said at least one channel is further defined as a jaw wire channel and a blade wire channel and said blade connection wire is disposed through said blade wire channel.

16. A tool cartridge defining a longitudinal axis and comprising:

a first jaw and a second jaw for grasping tissue therebetween wherein at least said first jaw is movable between an open position and a closed position;

said first jaw including an actuation portion and a grasping portion wherein said grasping portion extends longitudinally from said actuation portion;

a first jaw connection wire operatively connected to said actuation portion of said first jaw;

a substantially cylindrical sheath encompassing at least part of said first jaw connection wire, wherein a side portion of the substantially cylindrical sheath includes a longitudinal slit;

a grip disposed around at least part of said sheath and slidably engaging said sheath; and a piston disposed within said sheath and operatively connected to said grip such that said grip and piston move in relation with one another, said piston being connected to said grip by a pin slideable within said longitudinal slit of said sheath, wherein a slideable movement of said grip with respect to said sheath is limited by a slideable movement of said pin within said slit; and wherein said first jaw connection wire is operatively connected to said piston for moving said first jaw in response to movement of said grip.

17. A tool cartridge as set forth in claim 16 wherein said first jaw connection wire includes a longitudinal portion generally parallel to said longitudinal axis and a lateral portion generally perpendicular to said longitudinal axis.

18. A surgical apparatus as set forth in claim 17 wherein said lateral portion interfaces with a hole defined in said actuation portion of said first jaw.

19. A tool cartridge as set forth in claim 16 wherein the pin is substantially perpendicular to the longitudinal axis.

* * * * *